(12) United States Patent
Swearingen

(10) Patent No.: US 9,212,109 B2
(45) Date of Patent: Dec. 15, 2015

(54) CATALYTIC PROCESSES FOR MAKING HYDROMONOCHLOROFLUOROBUTANE AND HYDROMONOCHLOROFLUOROPENTANE COMPOUNDS

(71) Applicant: E I DU PONT DE NEMOURS AND COMPANY, Wilmington, DE (US)

(72) Inventor: Ekaterina N Swearingen, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/352,723

(22) PCT Filed: Oct. 5, 2012

(86) PCT No.: PCT/US2012/058981
§ 371 (c)(1),
(2) Date: Apr. 18, 2014

(87) PCT Pub. No.: WO2013/062733
PCT Pub. Date: May 2, 2013

(65) Prior Publication Data
US 2014/0303410 A1  Oct. 9, 2014

Related U.S. Application Data

(60) Provisional application No. 61/550,485, filed on Oct. 24, 2011.

(51) Int. Cl.
*C07C 17/20* (2006.01)
*C07C 17/25* (2006.01)
(Continued)

(52) U.S. Cl.
CPC .............. *C07C 17/07* (2013.01); *C07C 17/206* (2013.01); *C07C 17/25* (2013.01); *C07C 19/10* (2013.01)

(58) Field of Classification Search
CPC ...... C07C 17/20; C07C 17/202; C07C 17/206
See application file for complete search history.

(56) References Cited

U.S. PATENT DOCUMENTS

| 7,943,015 B2 | 5/2011 | Rao et al. |
| 2010/0105967 A1 | 4/2010 | Nappa |
| 2011/0237844 A1* | 9/2011 | Tung et al. ............ 570/151 |

FOREIGN PATENT DOCUMENTS

| EP | 0567872 A1 | 4/1993 |
| RU | 2010147002 A1 | 11/2010 |

(Continued)

OTHER PUBLICATIONS

International Search Report and Written Opinion, PCT/US2012/058981, mailed date Dec. 19, 2012.

(Continued)

*Primary Examiner* — Jafar Parsa
*Assistant Examiner* — Medhanit Bahta

(57) ABSTRACT

Disclosed is a process involving contacting a hydrohalobutane selected from the group consisting of $CF_2HCHClCH_2CCl_2H$, $CF_3CHClCH_2CCl_2H$, $CF_3CHClCH_2CCl_3$, $CF_3CClHCHFCCl_2H$ and $CF_3CClHCHFCCl_3$, with HF in a reaction zone in the presence of an antimony halide catalyst selected from $SbCl_5$ and $SbF_5$ to form a first product mixture containing a hydromonochlorofluorobutane. Also disclosed is a process involving contacting a hydrohalopentane selected from the group consisting of $CF_2HCHClCH_2CX_2CX_3$ and $CF_3CHClCH_2CX_2CX_3$, wherein each X is independently selected from the group consisting of F and Cl, and not all X are fluorines, with HF in a reaction zone in the presence of an antimony halide catalyst selected from $SbCl_5$ and $SbF_5$ to form a first product mixture containing a hydromonochlorofluoropentane. A compound of the formula $CF_3CHClCH_2CHF_2$ is also disclosed.

9 Claims, 2 Drawing Sheets

(51) Int. Cl.
*C07C 19/10* (2006.01)
*C07C 21/18* (2006.01)
*C07C 17/07* (2006.01)

(56) References Cited

FOREIGN PATENT DOCUMENTS

| RU | 2010147008 | A1 | 11/2010 |
| RU | 2010147009 | A1 | 11/2010 |
| WO | 9216674 | A2 | 10/1992 |
| WO | 9304025 | A1 | 3/1993 |
| WO | 2011119370 | A2 | 9/2011 |
| WO | 2011119388 | A2 | 9/2011 |

OTHER PUBLICATIONS

Henne, Directed Chlorination of Aliphatic Fluorides, Department of Chemistry at the Ohio State University, vol. 67, Nov. 1945.

* cited by examiner

CATALYTIC PROCESSES FOR MAKING HYDROMONOCHLOROFLUOROBUTANE AND HYDROMONOCHLOROFLUOROPENTANE COMPOUNDS

BACKGROUND

This disclosure relates in general to the catalytic fluorination processes of making hydromonochlorofluorobutane and hydromonochlorofluoropentane compounds in the presence of antimony halide catalysts.

HCFCs (hydrochlorofluorocarbons), such as hydromonochlorofluorobutane and hydromonochlorofluoropentane compounds, can be employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. They are also useful as intermediates to internal hydrofluorobutenes and internal hydrofluoropentenes which are potential candidates to replace HCFCs in the applications noted above. Internal hydrofluorobutenes and internal hydrofluoropentenes, such as $CF_3CH=CHCHF_2$ and $CF_3CH=CHCF_3$, are believed to be safe for the stratospheric ozone layer and have low global warming potentials (GWPs).

SUMMARY OF THE DISCLOSURE

The present disclosure provides a process comprising contacting a hydrohalobutane selected from the group consisting of $CF_2HCHClCH_2CCl_2H$, $CF_3CHClCH_2CCl_2H$, $CF_3CHClCH_2CCl_3$, $CF_3CClHCHFCCl_2H$ and $CF_3CClHCHFCCl_3$, with HF in a reaction zone in the presence of an antimony halide catalyst selected from $SbCl_5$ and $SbF_5$ to form a first product mixture comprising a hydromonochlorofluorobutane.

The present disclosure also provides a process comprising contacting a hydrohalopentane selected from the group consisting of $CF_2HCHClCH_2CX_2CX_3$ and $CF_3CHClCH_2CX_2CX_3$, wherein each X is independently selected from the group consisting of F and Cl, and not all X are fluorines, with HF in a reaction zone in the presence of an antimony halide catalyst selected from $SbCl_5$ and $SbF_5$ to form a first product mixture comprising a hydromonochlorofluoropentane.

The present disclosure also provides a new compound of the formula $CF_3CHClCH_2CHF_2$. It is particularly useful as an intermediate for producing an internal hydrofluorobutene of the formula $CF_3CH=CHCHF_2$.

DETAILED DESCRIPTION

Figure 1:
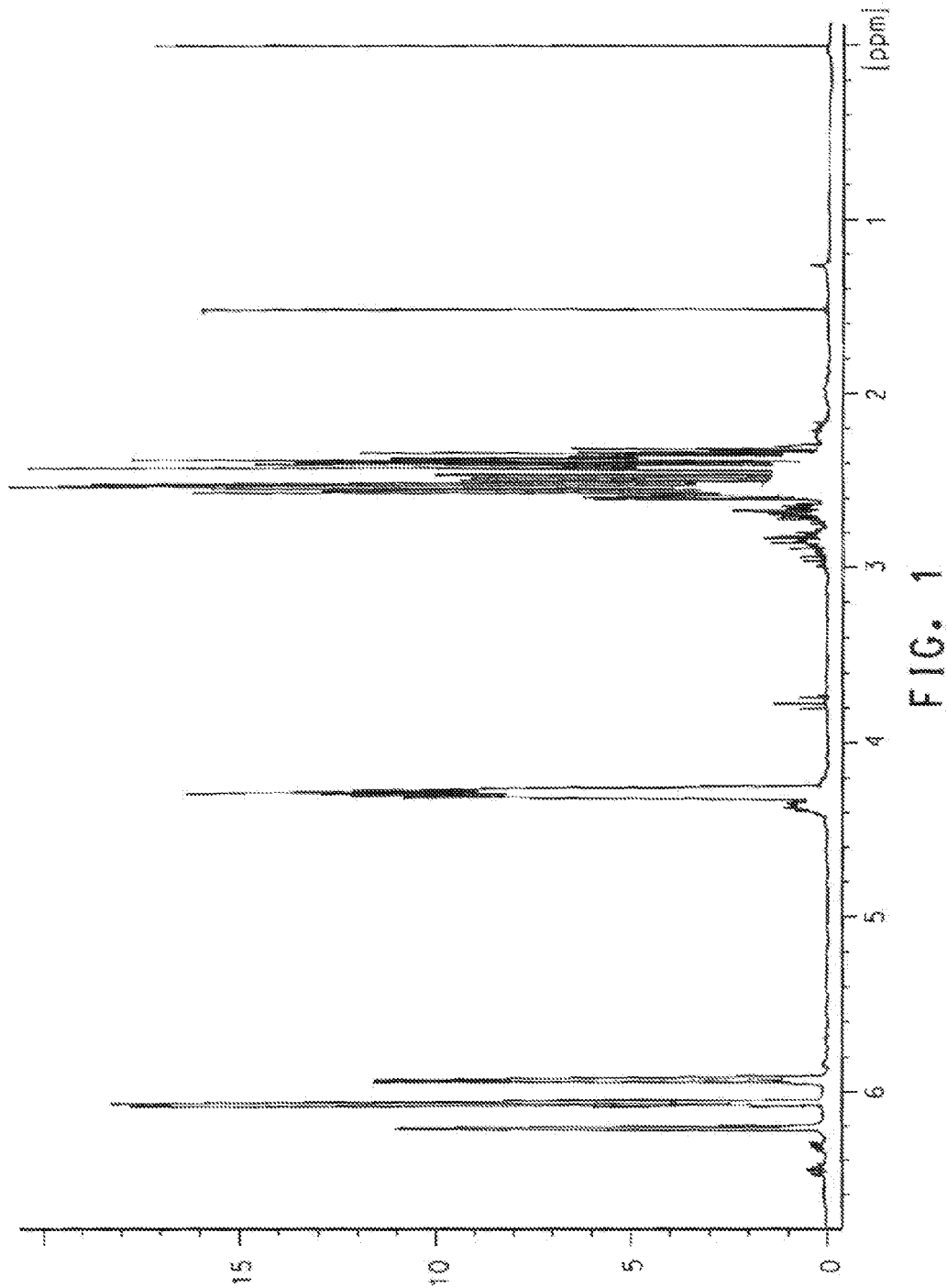
FIG. 1-FIG. 1 is a graphical representation of the $^1H$ NMR spectrum of $CF_3CHClCH_2CHF_2$.

The foregoing general description and the following detailed description are exemplary and explanatory only and are not restrictive of the inventive concept(s), as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "hydromonochlorofluorobutane", as used herein, means a n-butane wherein the hydrogens are partially substituted by some fluorines and one chlorine. Hydromonochlorofluorobutanes in this disclosure are selected from the group consisting of $CF_2HCHClCH_2CF_2H$, $CF_3CHClCH_2CHF_2$, $CF_3CHClCH_2CF_3$, $CF_3CClHCHFCF_2H$, and $CF_3CClHCHFCF_3$.

The term "hydromonochlorofluoropentane", as used herein, means a n-pentane wherein the hydrogens are partially substituted by some fluorines and one chlorine. Hydromonochlorofluoropentanes in this disclosure are selected from the group consisting of $CF_2HCHClCH_2CF_2CF_3$ and $CF_3CHClCH_2CF_2CF_3$.

The term "hydrohalobutane", as used herein, means a n-butane wherein the hydrogens are partially substituted by chlorines and fluorines. Hydrohalobutanes in this disclosure are selected from the group consisting of $CF_2HCHClCH_2CCl_2H$, $CF_3CHClCH_2CCl_2H$, $CF_3CHClCH_2CCl_3$, $CF_3CClHCHFCCl_2H$ and $CF_3CClHCHFCCl_3$.

The term "hydrohalopentane", as used herein, means a n-pentane wherein the hydrogens are partially substituted by chlorines and fluorines. Hydrohalopentanes in this disclosure are selected from the group consisting of $CF_2HCHClCH_2CX_2CX_3$ and $CF_3CHClCH_2CX_2CX_3$, wherein each X is independently selected from the group consisting of F and Cl, and not all X are fluorines.

The term "internal hydrofluorobutene", as used herein, means a partially fluorine-substituted butene wherein the carbon-carbon double bond is not at the terminal position. Internal hydrofluorobutenes in this disclosure are selected from the group consisting of $CF_2HCH=CHCF_2H$, $CF_3CH=CHCHF_2$, $CF_3CH=CHCF_3$, $CF_3CH=CFCF_2H$, and $CF_3CH=CFCF_3$.

The term "internal hydrofluoropentene", as used herein, means a partially fluorine-substituted pentene wherein the carbon-carbon double bond is not at the terminal position. Internal hydrofluoropentenes in this disclosure are selected from the group consisting of $CF_2HCH=CHCF_2CF_3$ and $CF_3CH=CHCF_2CF_3$.

The term "dehydrochlorinating", "dehydrochlorination" or "dehydrochlorinated", as used herein, means a process during which hydrogen and chlorine on adjacent carbons in a molecule are removed.

The internal hydrofluorobutenes and internal hydrofluoropentenes exist as different configurational isomers or stereoisomers. When the specific isomer is not designated, the present description is intended to include all single configurational isomers, single stereoisomers, or any combination thereof. For instance, $CF_3CH=CHCHF_2$ is meant to represent the E-isomer, Z-isomer, or any combination or mixture of both isomers in any ratio.

Hydrohalobutanes and hydrohalopentanes may be prepared by the processes known in the art Hydrohalobutanes and hydrohalopentanes may also be prepared by catalytic addition reactions of $CHCl_3$, $CCl_4$ or $CF_3CCl_3$ with suitable alkenes. For example, $CF_2CHClCH_2CCl_2H$ can be synthesized by addition reaction of $CHCl_3$ with $CF_2HCH=CH_2$; $CF_3CHClCH_2CCl_2H$ can be synthesized by addition reaction of $CHCl_3$ with $CF_3CH=CH_2$; $CF_3CHClCH_2CCl_3$ can be synthesized by addition reaction of $CCl_4$ with $CF_3CH=CH_2$; $CF_3CClHCHFCCl_2H$ can be synthesized by addition reaction of $CHCl_3$ with $CF_3CH=CHF$; $CF_3CClHCHFCCl_3$ can be synthesized by addition reaction of $CCl_4$ with $CF_3CH=CHF$; and $CF_3CHClCH_2CCl_2CF_3$ can be synthesized by addition reaction of $CF_3CCl_3$ with $CF_3CH=CH_2$. Suitable catalysts for such addition reactions include copper catalysts and iron catalysts. A copper catalyst typically comprises cupric chloride and a suitable reductant (e.g., copper powder, phenylhydrazine), and is typically used together with a solvent (e.g., acetonitrile). An iron catalyst typically comprises iron powder and ferric chloride, and is typically used together with a co-catalyst (e.g., tributyl phosphate). Further information on the preparation of hydrohalobutanes and hydrohalopentanes is provided in Russian Patent Application Numbers 2010147009, 2010147008 and 20100147002 [FL1564, FL1565 and FL1388].

Reactors, distillation columns, and their associated feed lines, effluent lines, and associated units used in applying the processes of embodiments of the inventive concept(s) described herein should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Fluorination Processes for Making Hydromonochlorofluorobutane or Hydromonochlorofluoropentane Compounds Disclosed is a process comprising contacting a hydrahalobutane selected from the group consisting of $CF_2HCHClCH_2CCl_2H$, $CF_3CHClCH_2CCl_2H$, $CF_3CHClCH_2CCl_3$, $CF_3CClHCHFCCl_2H$ and $CF_3CClHCHFCCl_3$, with HF in a reaction zone in the presence of an antimony halide catalyst selected from $SbCl_5$ and $SbF_5$ to form a first product mixture comprising a hydromonochlorofluorobutane. In some embodiments of this invention, the hydromonochlorofluorobutane is recovered from the first product mixture.

Also disclosed is a process comprising contacting a hydrohalopentane selected from the group consisting of $CF_2HCHClCH_2CX_2CX_3$ and $CF_3CHClCH_2CX_2CX_3$, wherein each X is independently selected from the group consisting of F and Cl, and not all X are fluorines, with HF in a reaction zone in the presence of an antimony halide catalyst selected from $SbCl_5$ and $SbF_5$ to form a first product mixture comprising a hydromonochlorofluoropentane. In some embodiments of this invention, the hydromonochlorofluoropentane is recovered from the first product mixture.

The processes above are fluorination processes for making hydromonochlorofluorobutane or hydromonochlorofluoropentane compounds. During the processes, the hydrohalobutane starting materials are selectively fluorinated to form hydromonochlorofluorobutane products, and the hydrohalopentane starting materials are selectively fluorinated to form hydromonochlorofluoropentane products.

In some embodiments of this invention, the hydrohalobutane starting material is $CF_2HCHClCH_2CCl_2H$, and the corresponding hydromonochlorofluorobutane product is $CF_2HCHClCH_2CF_2H$.

In some embodiments of this invention, the hydrohalobutane starting material is $CF_3CHClCH_2CCl_2H$, and the corresponding hydromonochlorofluorobutane product is $CF_3CHClCH_2CHF_2$.

In some embodiments of this invention, the hydrohalobutane starting material is $CF_3CHClCH_2CCl_3$, and the corresponding hydromonochlorofluorobutane product is $CF_3CHClCH_2CF_3$.

In some embodiments of this invention, the hydrohalobutane starting material is $CF_3CClHCHFCCl_2H$, and the corresponding hydromonochlorofluorobutane product is $CF_3CClHCHFCF_2H$.

In some embodiments of this invention, the hydrohalobutane starting material is $CF_3CClHCHFCCl_3$, and the corresponding hydromonochlorofluorobutane product is $CF_3CClHCHFCF_3$.

In some embodiments of this invention, the hydrohalopentane starting material is $CF_2HCHClCH_2CX_2CX_3$, and the corresponding hydromonochlorofluoropentane product is $CF_2HCHClCH_2CF_2CF_3$.

In some embodiments of this invention, the hydrohalopentane of the formula $CF_2HCHClCH_2CX_2CX_3$ is selected from the group consisting of $CF_2HCHClCH_2CCl_2CCl_3$, $CF_2HCHClCH_2CClFCCl_3$, $CF_2HCHClCH_2CCl_2CF_3$, $CF_2HCHClCH_2CClFCF_3$ and $CF_2HCHClCH_2CCl_2CClF_2$.

In some embodiments of this invention, the hydrohalopentane starting material is $CF_3CHClCH_2CX_2CX_3$, and the corresponding hydromonochlorofluoropentane product is $CF_3CHClCH_2CF_2CF_3$.

In some embodiments of this invention, the hydrohalopentane of the formula $CF_3CHClCH_2CX_2CX_3$ is selected from the group consisting of $CF_3CHClCH_2CCl_2CCl_3$, $CF_3CHClCH_2CClFCCl_3$, $CF_3CHClCH_2CCl_2CF_3$, $CF_3CHClCH_2CClFCF_3$ and $CF_3CHClCH_2CCl_2CClF_2$.

The term "antimony halide catalyst", as used herein, means $SbCl_5$ or $SbF_5$. $SbCl_5$ and $SbF_5$ are commercially available.

The fluorination process of this disclosure is typically carried out in anhydrous or substantially anhydrous conditions, which means that water, which is detrimental to the reaction, should be excluded as much as possible from the reaction zone.

Typically, the fluorination process of this disclosure is carried out in a liquid phase. It can be carried out in batch reactors, continuous reactors or any combination of such reactors by methods known in the art. In some embodiments of this invention, HF and antimony halide catalyst are pre-mixed before contacting or reacting with hydrohalobutane or hydrohalopentane. In some embodiments of this invention, hydrohalobutane or hydrohalopentane is fed to a reaction zone containing the mixture of HF and antimony halide catalyst. In some embodiments of this invention, hydrohalobutane or hydrohalopentane is co-fed with HF to a reaction zone containing the antimony halide catalyst.

The temperature employed in the reaction zone for the fluorination process of this disclosure typically ranges from about 60° C. to about 160° C. In some embodiments of this invention, the temperature employed in the reaction zone for the fluorination process of this disclosure ranges from about 80° C. to about 140° C. In some embodiments of this invention, the temperature employed in the reaction zone for the fluorination process of this disclosure ranges from about 100° C. to about 140° C.

The pressure in the reaction zone for the fluorination process of this disclosure can be subatmospheric, atmospheric or superatmospheric. In some embodiments of this invention, the fluorination process of this disclosure is conducted under autogenous pressure.

The fluorination process of this disclosure uses a molar ratio of HF to the hydrohalobutane or hydrohalopentane starting material that is at least stoichiometric. The stoichiometric amount is the total number of Cl substituents on the hydrohalobutane or hydrohalopentane starting materials minus one. For example, the stoichiometric ratio of HF to $CF_3CHClCH_2CCl_2H$ is 2:1.

The molar ratio of HF to the hydrohalobutane or hydrohalopentane starting material is typically from about the stoichiometric amount to about 50:1. In some embodiments of this invention, the molar ratio of HF to the hydrohalobutane or hydrohalopentane starting material is from about twice the stoichiometric amount to about 30:1. In some embodiments of this invention, the molar ratio of HF to the hydrohalobutane or hydrohalopentane starting material is from about twice the stoichiometric amount to about 20:1.

The hydromonochlorofluorobutane or hydromonochlorofluoropentane product can be recovered from its reaction product mixture by well-known techniques, such as fractional distillation.

At the end of the fluorination reaction, the reaction may be quenched with water or a buffer solution, such as a phosphate solution. The organic phase can be separated, dried and distilled to recover the hydromonochlorofluorobutane or hydromonochlorofluoropentane product. In some embodiments of this invention, the recovered hydromonochlorofluorobutane or hydromonochlorofluoropentane is at least 95 mole % pure. In some embodiments of this invention, the recovered hydromonochlorofluorobutane or hydromonochlorofluoropentane is at least 98 mole % pure.

Also disclosed is a new compound of the formula $CF_3CHClCH_2CHF_2$. This is a novel hydromonochlorofluorobutane compound which may be made by reacting $CF_3CHClCH_2CCl_2H$ with HF in the presence of an antimony halide catalyst as demonstrated by Examples 1-3.

Dehydrochlorination Processes for Making Internal Hydrofluorobutenes and Internal Hydrofluoropentenes The hydromonochlorofluorobutane formed in the fluorination process above can be further dehydrochlorinated to form a second product mixture comprising an internal hydrofluorobutene. In some embodiments of this invention, the hydromonochlorofluorobutane is $CF_3CHClCH_2CHF_2$, and the corresponding internal hydrofluorobutene product is $CF_3CH=CHCHF_2$. In some embodiments of this invention, the hydromonochlorofluorobutane is $CF_3CHClCH_2CF_3$, and the corresponding internal hydrofluorobutene product is $CF_3CH=CHCF_3$.

The hydromonochlorofluoropentane formed in the fluorination process above can also be further dehydrochlorinated to form a second product mixture comprising an internal hydrofluoropentene. In some embodiments of this invention, the hydromonochlorofluoropentane is $CF_3CHClCH_2CF_2CF_3$, and the corresponding internal hydrofluoropentene product is $CF_3CH=CHCF_2CF_3$.

In some embodiments of this invention, the dehydrochlorination process is carried out by pyrolyzing hydromonochlorofluorobutane to form a second product mixture comprising an internal hydrofluorobutene. In some embodiments of this invention, the dehydrochlorination process is carried out by pyrolyzing hydromonochlorofluoropentane to form a second product mixture comprising an internal hydrofluoropentene. The term "pyrolyzing" or "pyrolysis", as used herein, means chemical change produced by heating in the absence of catalyst. Suitable reactors for pyrolysis may be of any shape consistent with the process. In some embodiments of this invention, the reactor is a cylindrical tube, either straight or coiled. Heat is applied to the outside of the tube, with the chemical reaction taking place on the inside of the tube. Of note are pyrolysis reactors wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, has an open structure like that of Raschig Rings or other packings with a high free volume to avoid the accumulation of coke and to minimize pressure drop, and permits a generally free flow of gas. In some embodiments of this invention, the reactor packing is in cartridge disposition for ease of insertion and removal. In some embodiments of this invention, the pyrolysis temperature ranges from about 500° C. to about 700° C. Pyrolysis processes have also been disclosed in U.S. Patent Publication No. 2010-0105967, which is incorporated herein by reference.

The dehydrochlorination process can also be carried out in the presence of a dehydrochlorination catalyst. In some embodiments of this invention, hydromonochlorofluorobutane is dehydrochlorinated in the presence of a dehydrochlorination catalyst to form a second product mixture comprising an internal hydrofluorobutene. In some embodiments of this invention, hydromonochlorofluoropentane is dehydrochlorinated in the presence of a dehydrochlorination catalyst to form a second product mixture comprising an internal hydrofluoropentene. Suitable dehydrochlorination catalysts include carbon, metals (including elemental metals, metal oxides, metal halides, and/or other metal salts); alumina; fluorided alumina; aluminum fluoride; aluminum chlorofluoride; metals supported on alumina; metals supported on aluminum fluoride or chlorofluoride; magnesium fluoride supported on aluminum fluoride; metals supported on fluorided alumina; alumina supported on carbon; aluminum fluoride or chlorofluoride supported on carbon; fluorided alumina supported on carbon; metals supported on carbon; and mixtures of metals, aluminum fluoride or chlorofluoride, and graphite. Suitable metals for use on dehydrochlorination catalysts (optionally on alumina, aluminum fluoride, aluminum chlorofluoride, fluorided alumina, or carbon) include chromium, iron, and lanthanum. Typically, when used on a support, the total metal content of the dehydrochlorination catalyst will be from about 0.1 to 20 percent by weight; and in some embodiments from about 0.1 to 10 percent by weight. In some embodiments of this invention, dehydrochlorination catalysts include carbon, alumina, and fluorided alumina. In some embodiments of this invention, carbon includes acid-washed carbon, activated carbon and three dimensional matrix carbonaceous materials. The catalytic dehydrochlorination processes have also been disclosed in U.S. Pat. No. 7,943,015, which is incorporated herein by reference.

In some embodiments of this invention, the dehydrochlorination process is carried out by contacting hydromonochlorofluorobutane with a basic aqueous solution to form a second product mixture comprising an internal hydrofluorobutene. In some embodiments of this invention, the dehydrochlorination process is carried out by contacting hydromonochlorofluoropentane with a basic aqueous solution to form a second product mixture comprising an internal hydrofluoropentene. As used herein, the basic aqueous solution is a liquid that is primarily an aqueous liquid having a pH of over 7; and the liquid may be a solution, dispersion, emulsion, suspension or the like. In some embodiments of this invention, the basic aqueous solution has a pH of 8 or higher. In some embodiments of this invention, the basic aqueous solution has a pH of 10 or higher. In some embodiments of this invention, an inorganic base is used to form the basic aqueous solution. Such inorganic bases can be selected from the group consisting of hydroxide, oxide, carbonate, and phosphate salts of alkali, alkaline earth metals and mixtures thereof. In some embodiments, such inorganic base is sodium hydroxide, potassium hydroxide, or mixtures thereof. In some embodiments of this invention, the basic aqueous solution is an aqueous solution of a quaternary ammonium hydroxide of the formula $NR_4OH$ wherein each R is independently hydrogen, a $C_1$ to $C_{16}$ alkyl group, aralkyl group, or substituted alkyl group, provided that not all R are hydrogens. Examples of $NR_4OH$ compounds useful in this invention are tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, and choline hydroxide. Optionally, hydromonochlorofluorobutane or hydromonochlorofluoropentane is contacted with the basic aqueous solution in the presence of an organic solvent. In some embodiments of this invention, the organic solvent is selected from the group consisting of benzene and its derivatives, alcohols (e.g., methanol, ethanol, propanol, isopropanol, et al.), alkyl and aryl halides, alkyl and aryl nitriles, alkyl, alkoxy and aryl ethers, amides, ketones, sulfoxides, phosphate esters and mixtures thereof. Optionally, hydromonochlorofluorobutane or hydromonochlorofluoropentane is contacted with the basic aqueous solution in the presence of a phase transfer catalyst. As used herein, the term "phase transfer catalyst" is intended to mean a substance that facilitates the transfer of ionic compounds into an organic phase from an aqueous phase or from a solid phase. A phase transfer catalyst facilitates the reaction between water-soluble and water-insoluble reaction components. In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral. In some embodiments of this invention, onium salts include quaternary phosphonium salts and quaternary ammonium salts. Examples of quaternary ammonium salts include tetra-n-butylammonium hydroxide, tetramethylammonium chloride, tetramethylammonium bromide, benzyltriethylammonium chloride, methyltri-n-octylammonium chloride (also known as Aliquat™ 336), dodecyltrimethylammonium bromide, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride.

In some embodiments of this invention, the internal fluorobutene or internal fluoropentene product may be recovered from the product mixture by fractional distillation.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates that contacting $CF_3CHClCH_2CCl_2H$ with HF in the presence of $SbCl_5$ catalyst forms $CF_3CHClCH_2CF_2H$.

A 400 ml Hastelloy™ shaker tube was loaded with 42.8 g of $CF_3CHClCH_2CCl_2H$, 6 g of $SbCl_5$ and 50 g of HF. The shaker tube was heated to 80° C. and kept at this temperature for 8 hrs. Then the mixture was quenched with a phosphate buffer solution. The lower layer was separated and analyzed by GC/MS. The analysis indicated the formation of the desired novel hydromonochlorofluorbutane compound $CF_3CHClCH_2CF_2H$ with 31% conversion and 61 mole % selectivity. The separated lower layers from several batchs of the reactions were combined and distilled to give pure $CF_3CHClCH_2CF_2H$ with boiling point of 54-56° C.

Figure 2:
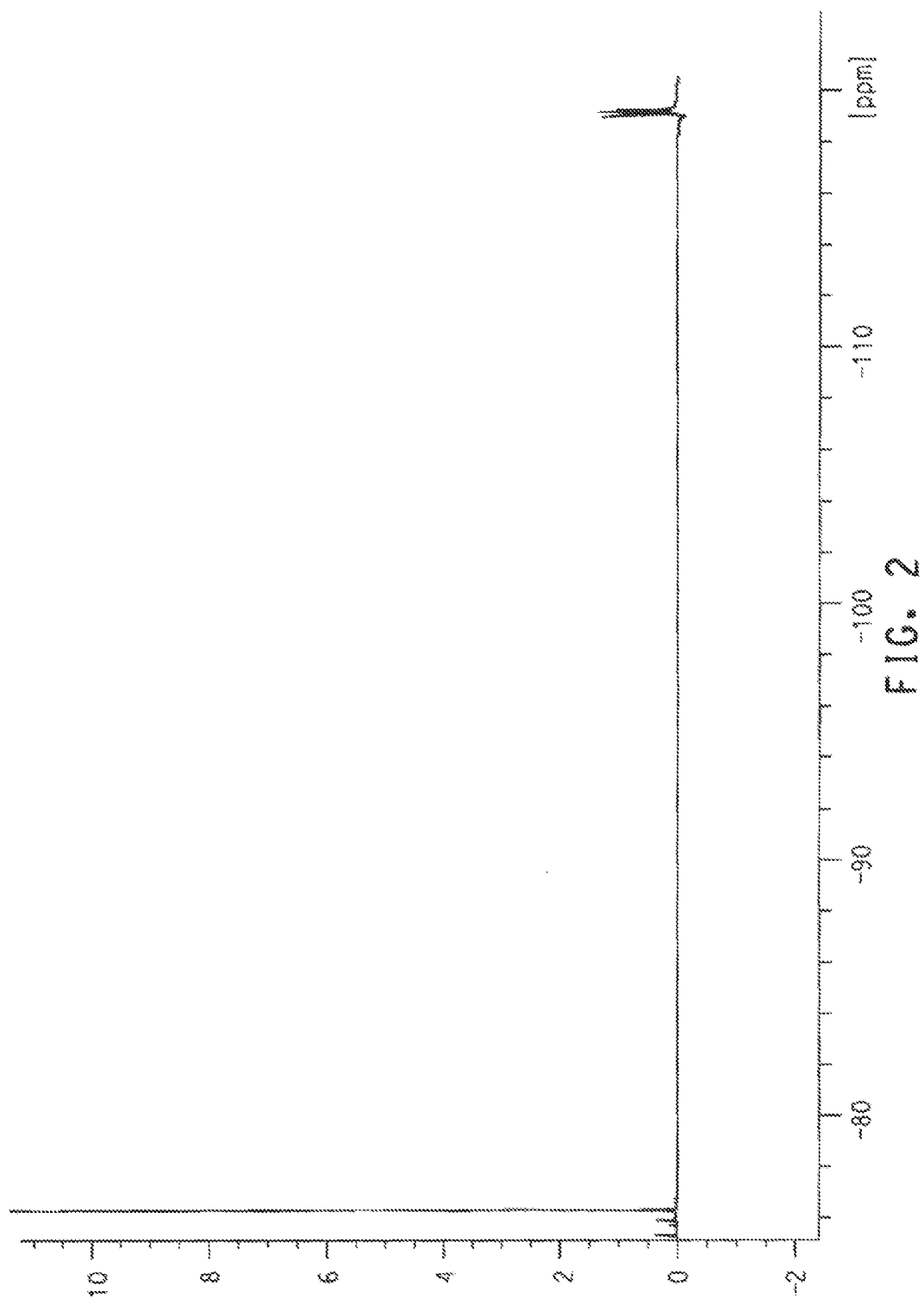
FIG. 2-FIG. 2 is a graphical representation of the $^{19}F$ NMR spectrum of $CF_3CHClCH_2CHF_2$.

$CF_3CHClCH_2CF_2H$ was further characterized by mass and NMRs. NMR spectrums are also shown in FIG. 1 and FIG. 2:
MS: 181, 162, 146, 127, 113, 95, 77, 69, 51.
$^1$H NMR ($CDCl_3$); 6.07 ppm 1H ($J^F$=55.6 Hz triplet, $J^H$=6.8 Hz, doublet, $J^H$=2.5 Hz, doublet); 4.3 ppm 1H, multiplet; 2.5 ppm 1H, multiplet, 2.4 ppm 1H, multiplet.
$^{19}$F NMR ($CDCl_3$): −76 ppm 3F ($J^H$=6.8 Hz, doublet); −119.26 ppm 2F, multiplet.

Example 2

Example 2 demonstrates that contacting $CF_3CHClCH_2CCl_2H$ with HF in the presence of $SbCl_5$ catalyst forms $CF_3CHClCH_2CF_2H$.

A 240 ml Hastelloy™ shaker tube was loaded with 21.4 g (0.1 mole) of $CF_3CHClCH_2CCl_2H$, 6 g (0.02 mole) of $SbCl_5$ and 24 g (1.2 mole) of HF. The shaker tube was heated to 120° C. and kept at this temperature for 5 hrs. Then the mixture was quenched with a phosphate buffer solution. The lower layer was separated and analyzed by GC/MS. The analysis indicated the formation of the desired novel hydromonochlorofluorbutane compound $CF_3CHClCH_2CF_2H$ with 65% conversion and 81 mole % selectivity.

Example 3

Example 3 demonstrates that contacting $CF_3CHClCH_2CCl_2H$ with HF in the presence of $SbF_5$ catalyst forms $CF_3CHClCH_2CF_2H$.

A 400 ml Hastelloy™ shaker tube was loaded with 21.4 g of $CF_3CHClCH_2CCl_2H$, 2.2 g of $SbF_5$ and 24 g of HF. The shaker tube was heated to 80° C. and kept at this temperature for 8 hrs. Then the mixture was quenched with a phosphate buffer solution. The lower layer was separated and analyzed by GC/MS. The analysis indicated the formation of the desired novel hydromonochlorofluorbutane compound $CF_3CHClCH_2CF_2H$ with 10% conversion and 20 mole % selectivity.

Example 4

Example 4 demonstrates that contacting $CF_3CHClCH_2CF_2H$ with a KOH solution in the presence of Aliquat™ 336 forms $CF_3CH=CHCF_2H$.

A 250 ml three-neck flask was equipped with thermocouple well, addition funnel, and short path distillation. The flask was charged with 30 ml of $H_2O$, 30 ml of isopropanol, 1.6 g of Aliquat™ 336, and 36.4 g (0.2 mole) of $CF_3CClHCH_2CHF_2$. The flask was heated to 40-45° C. The receiver for the short path distillation was cooled with dry-ice. A KOH solution (21 g (0.35 mole) of KOH dissolved in 40 g of water) was added dropwise to the flask. 28.9 g of the product mixture containing 38.9% of $CF_3CH=CHCF_2H$, 42.2% of $CF_3CHClCH_2CF_2H$ and 15% of isopropanol was collected in the receiver. The product mixture was distilled to give 7.5 g (0.05 mole) of $CF_3CH=CHCF_2H$ with boiling point of 31.1-34.6° C., and 13.4 g of $CF_3CHClCH_2CF_2H$. The conversion of the $CF_3CHClCH_2CF_2H$ starting material was 63%. The yield of the $CF_3CH=CHCF_2H$ product was 40 mole %. $CF_3CH=CHCF_2H$ above with boiling point of 31.1-34.6° C. was distilled again to give $CF_3CH=CHCF_2H$ with boiling point of 32.6-34.6° C. Analysis indicated that it contained both trans and cis isomers at the ratio of 6.8:1.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the inventive concept(s) as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising contacting a hydrohalopentane selected from the group consisting of $CF_2HCHClCH_2CX_2CX_3$ and $CF_3CHClCH_2CX_2CX_3$, wherein each X is independently selected from the group consisting of F and Cl, and not all X are fluorines, with HF in a reaction zone in the presence of an antimony halide catalyst selected from $SbCl_5$ and $SbF_5$ to form a first product mixture comprising a hydromonochlorofluoropentane.

2. The process of claim 1, further comprising recovering the hydromonochlorofluoropentane from the first product mixture.

3. The process of claim 1 wherein the hydrohalopentane is $CF_2HCHClCH_2CX_2CX_3$, and the hydromonochlorofluoropentane is $CF_2HCHClCH_2CF_2CF_3$.

4. The process of claim 3 wherein the hydrohalopentane is selected from the group consisting of $CF_2HCHClCH_2CCl_2CCl_3$, $CF_2HCHClCH_2CClFCCl_3$, $CF_2HCHClCH_2CCl_2CF_3$, $CF_2HCHClCH_2CClFCF_3$ and $CF_2HCHClCH_2CCl_2CClF_2$.

5. The process of claim 1 wherein the hydrohalopentane is $CF_3CHClCH_2CX_2CX_3$, and the hydromonochlorofluoropentane is $CF_3CHClCH_2CF_2CF_3$.

6. The process of claim 5 wherein the hydrohalopentane is selected from the group consisting of $CF_3CHClCH_2CCl_2CCl_3$, $CF_3CHClCH_2CClFCCl_3$, $CF_3CHClCH_2CCl_2CF_3$, $CF_3CHClCH_2CClFCF_3$ and $CF_3CHClCH_2CCl_2CClF_2$.

7. The process of claim 1, further comprising dehydrochlorinating the hydromonochlorofluoropentane to form a second product mixture comprising an internal hydrofluoropentene, wherein said dehydrochlorination step is selected from the group of steps consisting of:
a) pyrolyzing said hydromonochlorofluorobutane at a temperature of between about 500° C. and about 700° C.;
b) dehydrochlorinating hydromonochlorofluorobutane in the presence of a dehydrochlorination catalyst; and,
c) contacting hydromonochlorofluorobutane with a basic aqueous solution.

8. The process of claim 7 wherein the hydromonochlorofluoropentane is $CF_3CHClCH_2CF_2CF_3$, and the internal hydrofluoropentene is $CF_3CH=CHCF_2CF_3$.

9. A process comprising:
contacting a hydrohalobutane with HF in a reaction zone in the presence of an antimony halide catalyst selected from $SbCl_5$ and $SbF_5$ to form a first product mixture comprising a hydromonochlorofluorobutane; and,
dehydrochlorinating the hydromonochlorofluorobutane to form a second product mixture comprising an internal hydrofluorobutene,
wherein said dehydrochlorination step is selected from the group of steps consisting of:
a) pyrolyzing said hydromonochlorofluorobutane at a temperature of between about 500° C. and about 700° C.;
b) dehydrochlorinating hydromonochlorofluorobutane in the presence of a dehydrochlorination catalyst; and,
c) contacting hydromonochlorofluorobutane with a basic aqueous solution,
wherein the hydrohalobutane is $CF_3CHClCH_2CCl_2H$, the hydromonochlorofluorobutane is $CF_3CHClCH_2CHF_2$, and the internal hydrofluorobutene is $CF_3CH=CHCHF_2$.

* * * * *